US009364514B2

(12) United States Patent
Rebollo Garcia et al.

(10) Patent No.: US 9,364,514 B2
(45) **Date of Patent: *Jun. 14, 2016**

(54) ANTI-TUMOR ADJUVANT THERAPY

(71) Applicants: Universite Pierre et Marie Curie (Paris 6), Paris (FR); Institute Curie, Paris (FR)

(72) Inventors: Angelita Rebollo Garcia, Paris (FR); Fariba Nemati, Paris (FR); Didier Decaudin, Verrieres le Buisson (FR)

(73) Assignees: Institute Curie, Paris (FR); Universite Pierre et Marie Curie (Paris 6), Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/366,504

(22) PCT Filed: Dec. 27, 2012

(86) PCT No.: PCT/EP2012/076970

§ 371 (c)(1),
(2) Date: Jun. 18, 2014

(87) PCT Pub. No.: WO2013/098339

PCT Pub. Date: Jul. 4, 2013

(65) Prior Publication Data

US 2015/0030699 A1 Jan. 29, 2015

(30) Foreign Application Priority Data

Dec. 27, 2011 (EP) .................................... 11306785

(51) Int. Cl.

| | |
|---|---|
| ***C07K 7/08*** | (2006.01) |
| ***A61K 38/00*** | (2006.01) |
| ***A61K 38/10*** | (2006.01) |
| ***C07K 14/47*** | (2006.01) |
| ***C12N 9/64*** | (2006.01) |
| ***A61K 31/337*** | (2006.01) |
| ***A61K 31/513*** | (2006.01) |
| ***A61K 31/664*** | (2006.01) |
| ***A61K 31/704*** | (2006.01) |
| ***A61K 33/24*** | (2006.01) |

(52) U.S. Cl.

CPC ............... *A61K 38/10* (2013.01); *A61K 31/337* (2013.01); *A61K 31/513* (2013.01); *A61K 31/664* (2013.01); *A61K 31/704* (2013.01); *A61K 33/24* (2013.01); *C07K 7/08* (2013.01); *C07K 14/4747* (2013.01); *C12N 9/6475* (2013.01); *A61K 38/00* (2013.01); *C07K 2319/10* (2013.01)

(58) Field of Classification Search

CPC ... A61K 38/00; A61K 38/10; C07K 2319/70; C07K 7/08

USPC .......................................... 514/18.9; 530/324

See application file for complete search history.

(56) References Cited

U.S. PATENT DOCUMENTS

| | | | | |
|---|---|---|---|---|
| 6,890,721 B1 * | 5/2005 | Dixit .................... | C12N 9/6475 435/326 |
| 8,957,184 B2 * | 2/2015 | Rebollo Garcia .... | C12N 9/6475 530/324 |
| 2012/0021999 A1 * | 1/2012 | Rebollo Garcia .... | C12N 9/6475 514/19.6 |

FOREIGN PATENT DOCUMENTS

| | | |
|---|---|---|
| WO | WO-2004/011595 A2 | 2/2004 |
| WO | WO-2010/112471 A1 | 10/2010 |
| WO | WO-2012/042038 A2 | 4/2012 |

OTHER PUBLICATIONS

Garcia et al WO 2004/011595, published Feb. 5, 2004, machine translation, pp. 1-16.*

Nemati et al "Abstract A205: Targeting Caspase-9/PP2A Interaction as a New Antitumor Strategy", Molecular Cancer Therapeutics vol. 10, 2011.

Guergnon et al "Use of Penetrating Peptides Interacting with PP1/PP2A Proteins as a General Approach for a Drug Phosphatase Technology", Molecular Pharmacology vol. 69, pp. 1115-1124, 2006.

Guergnon et al "A PKA Survival Pathway Inhibited by DPT-PKI, a New Specific Cell Permeable PKA Inhibitor, is Induced by T. *Annulata* in Parasitized B-Lymphocytes", Apoptosis vol. 11, pp. 1263-1273, 2006.

* cited by examiner

*Primary Examiner* — Julie Ha

(74) *Attorney, Agent, or Firm* — Cesari and McKenna LLP

(57) ABSTRACT

A chimeric peptide construct having a cell penetrating peptide linked to a pro-apoptotic peptide. The construct can be used for treating a tumor in combination with an anti-tumor agent. Also disclosed is a method for treating a tumor with the chimeric peptide construct and a chemotherapeutic agent.

9 Claims, 5 Drawing Sheets

A

B

SEQUENCE LISTING

<160> NUMBER OF SEQ ID NOS: 42

<210> SEQ ID NO 1
<211> LENGTH: 18
<212> TYPE: PRT
<213> ORGANISM: Mus musculus

<400> SEQUENCE: 1

Tyr Ile Glu Thr Leu Asp Asp Ile Leu Glu Gln Trp Ala Arg Ser Glu
1 5 10 15

Asp Leu

<210> SEQ ID NO 2
<211> LENGTH: 18
<212> TYPE: PRT
<213> ORGANISM: Homo sapiens

<400> SEQUENCE: 2

Tyr Val Glu Thr Leu Asp Asp Ile Phe Glu Gln Trp Ala His Ser Glu
1 5 10 15

-continued

```
Asp Leu


<210> SEQ ID NO 3
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MISC_FEATURE
<222> LOCATION: (2)..(2)
<223> OTHER INFORMATION: Xaa is valine or isoleucine
<220> FEATURE:
<221> NAME/KEY: MISC_FEATURE
<222> LOCATION: (7)..(7)
<223> OTHER INFORMATION: Xaa is aspartic acid or glycine
<220> FEATURE:
<221> NAME/KEY: MISC_FEATURE
<222> LOCATION: (9)..(9)
<223> OTHER INFORMATION: Xaa is phenylalanine or leucine
<220> FEATURE:
<221> NAME/KEY: MISC_FEATURE
<222> LOCATION: (14)..(14)
<223> OTHER INFORMATION: Xaa is arginine or histidine
<220> FEATURE:
<221> NAME/KEY: MISC_FEATURE
<222> LOCATION: (16)..(16)
<223> OTHER INFORMATION: Xaa is vacant or is glutamate, or glutamate-
      aspartate, or glutamate-aspartate-leucine

<400> SEQUENCE: 3

Tyr Xaa Glu Thr Leu Asp Xaa Ile Xaa Glu Gln Trp Ala Xaa Ser Xaa
1               5                   10                  15


<210> SEQ ID NO 4
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MISC_FEATURE
<222> LOCATION: (1)..(1)
<223> OTHER INFORMATION: Xaa is lysine or valine-lysine
<220> FEATURE:
<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is vacant, is lysine or lysine-isoleucine
<220> FEATURE:
<221> NAME/KEY: MISC_FEATURE
<222> LOCATION: (11)..(11)
<223> OTHER INFORMATION: Xaa is vacant or is an amino acid sequence of
      one to 4 amino acids

<400> SEQUENCE: 4

Xaa Lys Lys Lys Ile Lys Xaa Glu Ile Xaa Xaa
1               5                   10


<210> SEQ ID NO 5
<211> LENGTH: 18
<212> TYPE: PRT
<213> ORGANISM: Artificial Sequence
<220> FEATURE:
<223> OTHER INFORMATION: cell penetrating peptide

<400> SEQUENCE: 5

Arg Gln Lys Arg Leu Ile Arg Gln Lys Arg Leu Ile Arg Gln Lys Arg
1               5                   10                  15
```

Leu Ile

<210> SEQ ID NO 6
<211> LENGTH: 18
<212> TYPE: PRT
<213> ORGANISM: Artificial Sequence
<220> FEATURE:
<223> OTHER INFORMATION: cell penetrating peptide

<400> SEQUENCE: 6

Arg His Ser Arg Ile Gly Arg His Ser Arg Ile Gly Arg His Ser Arg
1               5                   10                  15

Ile Gly

<210> SEQ ID NO 7
<211> LENGTH: 16
<212> TYPE: PRT
<213> ORGANISM: Artificial Sequence
<220> FEATURE:
<223> OTHER INFORMATION: cell penetrating peptide

<400> SEQUENCE: 7

Arg His Ser Arg Ile Gly Ile Ile Gln Gln Arg Arg Thr Arg Asn Gly
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: cell penetrating peptide

<400> SEQUENCE: 8

Arg His Ser Arg Ile Gly Val Thr Arg Gln Arg Arg Ala Arg Asn Gly
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: cell penetrating peptide

<400> SEQUENCE: 9

Arg Arg Arg Arg Arg Arg Arg Ser Arg Gly Arg Arg Arg Thr Tyr
1               5                   10                  15

<210> SEQ ID NO 10
<211> LENGTH: 9
<212> TYPE: PRT
<213> ORGANISM: Human immunodeficiency virus

<400> SEQUENCE: 10

Arg Lys Lys Arg Arg Gln Arg Arg Arg
1               5

<210> SEQ ID NO 11
<211> LENGTH: 11
<212> TYPE: PRT
<213> ORGANISM: Human immunodeficiency virus

<400> SEQUENCE: 11

Tyr Gly Arg Lys Lys Arg Arg Gln Arg Arg Arg
1               5                   10

<210> SEQ ID NO 12
<211> LENGTH: 9
<212> TYPE: PRT
<213> ORGANISM: Artificial Sequence
<220> FEATURE:
<223> OTHER INFORMATION: cell penetrating peptide

<400> SEQUENCE: 12

```
Arg Arg Arg Arg Arg Arg Arg Arg Arg
1               5
```

<210> SEQ ID NO 13
<211> LENGTH: 11
<212> TYPE: PRT
<213> ORGANISM: Artificial Sequence
<220> FEATURE:
<223> OTHER INFORMATION: cell penetrating peptide

<400> SEQUENCE: 13

```
Arg Arg Arg Arg Arg Arg Arg Arg Arg Arg Arg
1               5                   10
```

<210> SEQ ID NO 14
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 14

```
Gly Leu Phe Glu Ala Ile Glu Gly Phe Ile Glu Asn Gly Trp Glu Gly
1               5                   10                  15

Met Ile Asp Gly Trp Tyr Gly Arg Arg Arg Arg Arg Arg Arg Arg Arg
            20                  25                  30
```

<210> SEQ ID NO 15
<211> LENGTH: 16
<212> TYPE: PRT
<213> ORGANISM: Drosophila

<400> SEQUENCE: 15

```
Arg Gln Ile Lys Ile Trp Phe Gln Asn Arg Arg Met Lys Trp Lys Lys
1               5                   10                  15
```

<210> SEQ ID NO 16
<211> LENGTH: 27
<212> TYPE: PRT
<213> ORGANISM: Artificial Sequence
<220> FEATURE:
<223> OTHER INFORMATION: cell penetrating peptide

<400> SEQUENCE: 16

```
Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25
```

<210> SEQ ID NO 17
<211> LENGTH: 33
<212> TYPE: PRT
<213> ORGANISM: Maurus Palmatus

<400> SEQUENCE: 17

```
Gly Asp Cys Leu Pro His Leu Lys Leu Cys Lys Glu Asn Lys Asp Cys
1               5                   10                  15
```

Cys Ser Lys Lys Cys Lys Arg Arg Gly Thr Asn Ile Glu Lys Arg Cys
20 25 30

Arg

<210> SEQ ID NO 18
<211> LENGTH: 10
<212> TYPE: PRT
<213> ORGANISM: Artificial Sequence
<220> FEATURE:
<223> OTHER INFORMATION: cell penetrating peptide

<400> SEQUENCE: 18

Lys Lys Lys Lys Lys Lys Lys Lys Lys Lys
1 5 10

<210> SEQ ID NO 19
<211> LENGTH: 11
<212> TYPE: PRT
<213> ORGANISM: Human immunodeficiency virus

<400> SEQUENCE: 19

Tyr Ala Arg Ala Ala Ala Arg Gln Ala Arg Ala
1 5 10

<210> SEQ ID NO 20
<211> LENGTH: 12
<212> TYPE: PRT
<213> ORGANISM: Hepatitis B virus

<400> SEQUENCE: 20

Pro Leu Ser Ser Ile Phe Ser Arg Ile Gly Asp Pro
1 5 10

<210> SEQ ID NO 21
<211> LENGTH: 28
<212> TYPE: PRT
<213> ORGANISM: Mus musculus

<400> SEQUENCE: 21

Met Ala Asn Leu Gly Tyr Trp Leu Leu Ala Leu Phe Val Thr Met Trp
1 5 10 15

Thr Asp Val Gly Leu Cys Lys Lys Arg Pro Lys Pro
20 25

<210> SEQ ID NO 22
<211> LENGTH: 35
<212> TYPE: PRT
<213> ORGANISM: Homo sapiens

<400> SEQUENCE: 22

Gly Gly Gly Ala Arg Lys Lys Ala Ala Lys Ala Ala Arg Lys Lys Ala
1 5 10 15

Ala Lys Ala Ala Arg Lys Lys Ala Ala Lys Ala Ala Arg Lys Lys Ala
20 25 30

Ala Lys Ala
35

<210> SEQ ID NO 23
<211> LENGTH: 19
<212> TYPE: PRT
<213> ORGANISM: Mus musculus

<400> SEQUENCE: 23

-continued

Leu Leu Ile Ile Leu Arg Arg Arg Arg Ile Arg Lys Gln Ala His Ala
1 5 10 15

His Ser Lys

<210> SEQ ID NO 24
<211> LENGTH: 23
<212> TYPE: PRT
<213> ORGANISM: Homo sapiens

<400> SEQUENCE: 24

Leu Ile Arg Leu Trp Ser His Leu Ile His Ile Trp Phe Gln Asn Arg
1 5 10 15

Arg Leu Lys Trp Lys Lys Lys
20

<210> SEQ ID NO 25
<211> LENGTH: 22
<212> TYPE: PRT
<213> ORGANISM: Avian infectious bursal disease virus

<400> SEQUENCE: 25

Thr Pro Trp Trp Arg Leu Trp Thr Lys Trp His His Lys Arg Arg Asp
1 5 10 15

Leu Pro Arg Lys Pro Glu
20

<210> SEQ ID NO 26
<211> LENGTH: 20
<212> TYPE: PRT
<213> ORGANISM: Artificial Sequence
<220> FEATURE:
<223> OTHER INFORMATION: cell penetrating peptide

<400> SEQUENCE: 26

Gly Leu Trp Arg Ala Leu Trp Arg Leu Leu Arg Ser Leu Trp Arg Leu
1 5 10 15

Leu Trp Arg Ala
20

<210> SEQ ID NO 27
<211> LENGTH: 24
<212> TYPE: PRT
<213> ORGANISM: Homo sapiens

<400> SEQUENCE: 27

Asp Ser His Ala Lys Arg His His Gly Tyr Lys Arg Lys Phe His Glu
1 5 10 15

Lys His His Ser His Arg Gly Tyr
20

<210> SEQ ID NO 28
<211> LENGTH: 16
<212> TYPE: PRT
<213> ORGANISM: Artificial Sequence
<220> FEATURE:
<223> OTHER INFORMATION: cell penetrating peptide

<400> SEQUENCE: 28

Lys Lys Lys Glu Glu Arg Ala Asp Leu Ile Ala Tyr Leu Lys Lys Ala
1 5 10 15

<210> SEQ ID NO 29
<211> LENGTH: 30

-continued

<212> TYPE: PRT
<213> ORGANISM: Artificial Sequence
<220> FEATURE:
<223> OTHER INFORMATION: cell penetrating peptide

<400> SEQUENCE: 29

```
Val Lys Lys Lys Lys Ile Lys Arg Glu Ile Lys Ile Tyr Val Glu Thr
1               5                   10                  15

Leu Asp Asp Ile Phe Glu Gln Trp Ala His Ser Glu Asp Leu
            20                  25                  30
```

<210> SEQ ID NO 30
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 30

```
Val Lys Lys Lys Lys Ile Lys Arg Glu Ile Lys Ile Tyr Ile Glu Thr
1               5                   10                  15

Leu Asp Asp Ile Leu Glu Gln Trp Ala Arg Ser Glu Asp Leu
            20                  25                  30
```

<210> SEQ ID NO 31
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 31

```
Val Lys Lys Lys Lys Ile Lys Ala Glu Ile Lys Ile Tyr Val Glu Thr
1               5                   10                  15

Leu Asp Asp Ile Phe Glu Gln Trp Ala His Ser Glu Asp Leu
            20                  25                  30
```

<210> SEQ ID NO 32
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 32

```
Val Lys Lys Lys Lys Ile Lys Ala Glu Ile Lys Ile Tyr Ile Glu Thr
1               5                   10                  15

Leu Asp Asp Ile Leu Glu Gln Trp Ala Arg Ser Glu Asp Leu
            20                  25                  30
```

<210> SEQ ID NO 33
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 33

```
Val Lys Lys Lys Lys Ile Lys Lys Glu Ile Lys Ile Tyr Val Glu Thr
1               5                   10                  15

Leu Asp Asp Ile Phe Glu Gln Trp Ala His Ser Glu Asp Leu
            20                  25                  30
```

<210> SEQ ID NO 34

-continued

<211> LENGTH: 30
<212> TYPE: PRT
<213> ORGANISM: Artificial Sequence
<220> FEATURE:
<223> OTHER INFORMATION: cell penetrating peptide

<400> SEQUENCE: 34

Val Lys Lys Lys Lys Ile Lys Lys Glu Ile Lys Ile Tyr Ile Glu Thr
1               5                   10                  15

Leu Asp Asp Ile Leu Glu Gln Trp Ala Arg Ser Glu Asp Leu
            20                  25                  30

<210> SEQ ID NO 35
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 35

Val Lys Lys Lys Lys Ile Lys Asn Glu Ile Lys Ile Tyr Val Glu Thr
1               5                   10                  15

Leu Asp Asp Ile Phe Glu Gln Trp Ala His Ser Glu Asp Leu
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 36

Val Lys Lys Lys Lys Ile Lys Asn Glu Ile Lys Ile Tyr Ile Glu Thr
1               5                   10                  15

Leu Asp Asp Ile Leu Glu Gln Trp Ala Arg Ser Glu Asp Leu
            20                  25                  30

<210> SEQ ID NO 37
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MISC_FEATURE
<222> LOCATION: (1)..(1)
<223> OTHER INFORMATION: Xaa is vacant, is a lysine, or valine-lysine
<220> FEATURE:
<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is vacant, is a lysine, or lysine-
      isoleucine

<400> SEQUENCE: 37

Xaa Lys Lys Lys Ile Lys Xaa Glu Ile Xaa
1               5                   10

<210> SEQ ID NO 38
<211> LENGTH: 12
<212> TYPE: PRT
<213> ORGANISM: Artificial Sequence
<220> FEATURE:
<223> OTHER INFORMATION: cell penetrating peptide -continued
<220> FEATURE:
<221> NAME/KEY: MISC_FEATURE
<222> LOCATION: (8)..(8)
<223> OTHER INFORMATION: Xaa is any amino acid

<400> SEQUENCE: 38

Val Lys Lys Lys Lys Ile Lys Xaa Glu Ile Lys Ile
1 5 10

<210> SEQ ID NO 39
<211> LENGTH: 12
<212> TYPE: PRT
<213> ORGANISM: Artificial sequence
<220> FEATURE:
<223> OTHER INFORMATION: cell penetrating peptide

<400> SEQUENCE: 39

Val Lys Lys Lys Lys Ile Lys Arg Glu Ile Lys Ile
1 5 10

<210> SEQ ID NO 40
<211> LENGTH: 12
<212> TYPE: PRT
<213> ORGANISM: Artificial sequence
<220> FEATURE:
<223> OTHER INFORMATION: cell penetrating peptide

<400> SEQUENCE: 40

Val Lys Lys Lys Lys Ile Lys Ala Glu Ile Lys Ile
1 5 10

<210> SEQ ID NO 41
<211> LENGTH: 12
<212> TYPE: PRT
<213> ORGANISM: Artificial sequence
<220> FEATURE:
<223> OTHER INFORMATION: cell penetrating peptide

<400> SEQUENCE: 41

Val Lys Lys Lys Lys Ile Lys Lys Glu Ile Lys Ile
1 5 10

<210> SEQ ID NO 42
<211> LENGTH: 12
<212> TYPE: PRT
<213> ORGANISM: Artificial sequence
<220> FEATURE:
<223> OTHER INFORMATION: cell penetrating peptide

<400> SEQUENCE: 42

Val Lys Lys Lys Lys Ile Lys Asn Glu Ile Lys Ile
1 5 10

ANTI-TUMOR ADJUVANT THERAPY

CROSS REFERENCE TO RELATED APPLICATIONS

Figure 1:
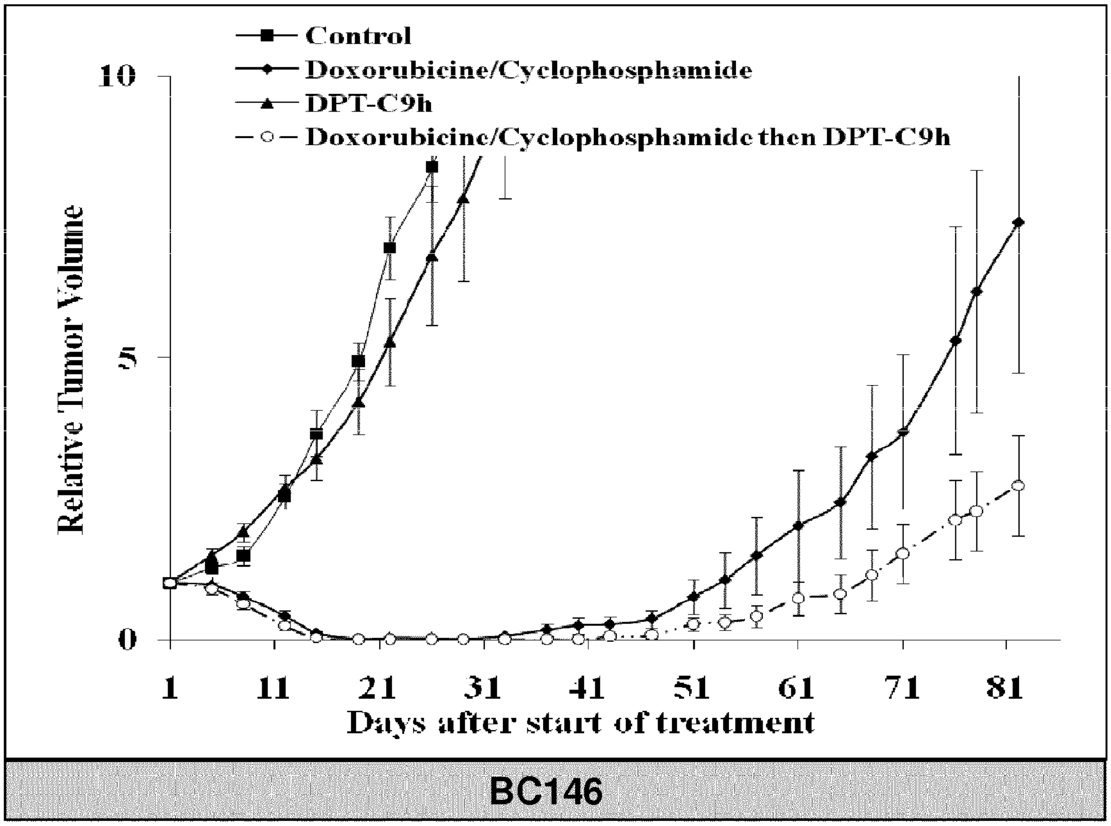

This application is the National Stage of International Application No. PCT/EP2012/076970, filed on Dec. 27, 2012, which claims the benefit of European Application No. 11306785.4, filed on Dec. 27, 2011. The contents of both applications are hereby incorporated by reference in their entirety.

The invention relates to the use of certain caspase 9 fragments as adjuvant in cancer treatment.

BACKGROUND OF THE INVENTION

Apoptosis is a genetically programmed cell death and its deregulation is associated among other pathologies, with cancer. While apoptosis is known to rely on the Bcl-2 family members and caspases, recent data suggested that two major families of serine/threonine phosphatases, PP1 and PP2A, are key actors involved in cell life or cell death decision. The Ser/Thre phosphatase PP2A has been implicated in both, induction and prevention of apoptosis, pointing to a complex interplay of phosphatase actions. Several phosphatases have recently become attractive targets for the treatment of a variety of diseases, including cancers. However, the only clinical drugs targeting a phosphatase are the immunosuppressive cyclosporine A and FK506.

International patent application WO2010/112471 discloses that PP2A interacts with caspase-9, and that a particular sequence from the C-terminal portion of caspase-9 protein is a PP2Ac binding domain. This sequence was identified as being YIETLDDILEQWARSEDL (SEQ ID NO: 1) for murine caspase-9, and as being YVETLDDIFEQWAHSEDL (SEQ ID NO: 2) for human caspase-9. This binding domain to PP2Ac corresponds to amino acid positions 401-418 of murine caspase-9 (NCBI accession number NP_056548), amino acid positions 363-380 of human caspase-9 (NCBI accession number NP_001220).

It was further demonstrated that this caspase-9 PPA2c-binding domain, when fused to a penetrating peptide (fusion peptide DPT-C9 and DPT-C9h), becomes a therapeutic molecule able to deregulate survival of human cells.

SUMMARY OF THE INVENTION

The inventors have now found that these caspase-9 fragments were especially efficient in tumor treatment when they were used as adjuvants to chemotherapy or hormonotherapy. They have more particularly shown a synergistic effect of the combined treatment of tumors with chimeric peptide constructs and chemotherapy or hormonotherapy, making it possible to reduce the dosage, and hence the toxic side effects, of the chemotherapeutic agent, or the hormone or hormone analog.

The present invention provides chimeric peptide construct comprising a cell penetrating peptide linked to a pro-apoptotic peptide, for use in treating a tumor in combination with an anti-tumor agent, preferably a chemotherapeutic agent, wherein the pro-apoptotic peptide comprises sequence (SEQ ID NO: 3)

$$Y\text{-}X_{4a}\text{-}ETLD\text{-}X_{4b}\text{-}I\text{-}X_5\text{-}EQWA\text{-}X_6\text{-}S\text{-}X_7$$

wherein $X_{4a}$ is valine or isoleucine;

$X_{4b}$ is aspartic acid or glycine;

$X_5$ is phenylalanine or leucine;

$X_6$ is arginine or histidine;

$X_7$ is vacant or is glutamate, or glutamate-aspartate, or glutamate-aspartate-leucine; or a proteolysis-resistant peptide deriving from said pro-apoptotic peptide by one or more chemical modifications, or a substantially homologous peptide, preferably deriving from SEQ ID NO:3 by one or more conservative substitutions, Said cell-penetrating peptide may preferably be (SEQ ID NO: 4)

$$X_1\text{-}KKKIK\text{-}\Psi\text{-}EI\text{-}X_2\text{-}X_3$$

wherein $X_1$ is vacant, is a lysine residue, or valine-lysine;

$X_2$ is vacant, is a lysine residue, or lysine-isoleucine;

$X_3$ is vacant or is an amino acid sequence of one to 4 amino acids;

and $\psi$ is any amino-acid;

or a proteolysis-resistant peptide deriving from SEQ ID NO:4 by one or more chemical modifications, or a substantially homologous peptide deriving from SEQ ID NO:4 by one or more conservative substitutions.

A further subject of the invention is a nucleic acid that encodes the chimeric peptide construct as herein, or a vector comprising said nucleic acid, for use in treating a tumor in combination with an anti-tumor agent, preferably a chemotherapeutic agent.

DETAILED DESCRIPTION OF THE INVENTION

Definitions

The term "patient" refers to a human or non human animal, preferably a mammal, including male, female, adult and children in need of a treatment wherein a pro-apoptotic effect is desired.

As used herein, the term "treatment" or "therapy" includes curative and/or prophylactic treatment. More particularly, curative treatment refers to any of the alleviation, amelioration and/or elimination, reduction and/or stabilization (e.g., failure to progress to more advanced stages) of a symptom, as well as delay in progression of a symptom of a particular disorder.

Prophylactic treatment refers to any of: halting the onset, reducing the risk of development, reducing the incidence, delaying the onset, reducing the development, as well as increasing the time to onset of symptoms of a particular disorder.

The term "penetrating peptide" or "cell-penetrating peptide" (or "CPP") or "shuttle peptide", as used interchangeably, means that the peptide is able to translocate into cells without causing substantial membrane damage, and can be used as a vector of other molecules when linked to them. The terms refer to cationic cell penetrating peptides, also called transport peptides, carrier peptides, or peptide transduction domains. The CPP, as shown herein, have the capability of inducing cell penetration of a peptide fused to the CPP within 30%, 40%, 50%, 60%, 70%, 80%, 90%, or 100% of cells of a given cell culture population, including all integers in between, and allow macromolecular translocation within multiple tissues in vivo upon systemic administration. A cell-penetrating peptide may also refers to a peptide which, when brought into contact with a cell under appropriate conditions, passes from the external environment in the intracellular environment, including the cytoplasm, organelles such as mitochondria, or the nucleus of the cell, in conditions significantly greater than passive diffusion. This property may be assessed by various methods known by the skilled person.

Two amino acid sequences are "homologous", "substantially homologous" or "substantially similar" when one or more amino acid residue are replaced by a biologically similar residue or when greater than 80% of the amino acids are identical, or greater than about 90%, preferably greater than about 95%, are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs known in the art (BLAST, FASTA, etc.). Preferably, these homologous peptides do not include two cysteine residues, so that cyclization is prevented.

The term "conservative substitution" as used herein denotes the replacement of an amino acid residue by another, without altering the overall conformation and function of the peptide, including, but not limited to, replacement of an amino acid with one having similar properties (such as, for example, polarity, hydrogen bonding potential, acidic, basic, shape, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Neutral hydrophilic amino acids, which can be substituted for one another, include asparagine, glutamine, serine and threonine.

By "substituted" or "modified" the present invention includes those amino acids that have been altered or modified from naturally occurring amino acids.

As such, it should be understood that in the context of the present invention, a conservative substitution is recognized in the art as a substitution of one amino acid for another amino acid that has similar properties. Examples of conservative substitutions are set out in the Table 1 below:

TABLE 1

Conservative Substitutions I

| SIDE CHAIN CHARACTERISTIC | AMINO ACID |
|---|---|
| Non-polar | G A P I L V |
| Polar-uncharged | C S T M N Q |
| Polar-charged | D E K R |
| Aromatic | H F W Y |
| Other | N Q D E |

Alternatively, conservative amino acids can be grouped as described in Lehninger, 1975, as set out in Table 2, immediately below.

TABLE 2

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

As still another alternative, exemplary conservative substitutions are set out in Table 3, immediately below.

TABLE 3

Conservative Substitutions III

| Original Residue | Exemplary Substitution |
|---|---|
| Ala (A) | Val (V), Leu (L), Ile (I) |
| Arg (R) | Lys (K), Gln (Q), Asn (N) |
| Asn (N) | Gln (Q), His (H), Lys (K), Arg (R) |
| Asp (D) | Glu (E) |
| Cys (C) | Ser (S) |
| Gln (Q) | Asn (N) |
| Glu (E) | Asp (D) |
| His (H) | Asn (N), Gln (Q), Lys (K), Arg (R) |
| Ile (I) | Leu (L), Val (V), Met (M), Ala (A), Phe (F) |
| Leu (L) | Ile (I), Val (V), Met (M), Ala (A), Phe (F) |
| Lys (K) | Arg (R), Gln (Q), Asn (N) |
| Met (M) | Leu (L), Phe (F), Ile (I) |
| Phe (F) | Leu (L), Val (V), Ile (I), Ala (A) |
| Pro (P) | Gly (G) |
| Ser (S) | Thr (T) |
| Thr (T) | Ser (S) |
| Trp (W) | Tyr (T) |
| Tyr (Y) | Trp (W), Phe (F), Thr (T), Ser (S) |
| Val (V) | Ile (I), Leu (L), Met (M), Phe (F), Ala (A) |

Pro-Apoptotic Peptide:

The invention makes use of a pro-apoptotic peptide that is a fragment of caspase-9 protein, or derives therefrom.

According to one embodiment, the pro-apoptotic peptide comprises, or consists in the following amino acid sequence:

(SEQ ID NO: 3)

$Y\text{-}X_{4a}\text{-}ETLD\text{-}X_{4b}\text{-}I\text{-}X_5\text{-}EQWA\text{-}X_6\text{-}S\text{-}X_7$ wherein $X_{4a}$ is valine or isoleucine;

$X_{4b}$ is aspartic acid or glycine;

$X_5$ is phenylalanine or leucine;

$X_6$ is arginine or histidine;

$X_7$ is vacant or is glutamate, or glutamate-aspartate, or glutamate-aspartate-leucine; or a proteolysis-resistant peptide deriving from said pro-apoptotic peptide by one or more chemical modifications, or a substantially homologous peptide, preferably deriving from SEQ ID NO:3 by one or more conservative substitutions.

Such proteolysis-resistant or homologous peptides induce cell apoptosis, in vitro and/or in vivo. Assays for determining if a molecule, for instance a peptide, induces cell apoptosis are well-known in the art and include, for instance, incubating cells with the candidate peptide and determining if apoptosis is induced by said candidate peptide, e.g. by Annexin V and PI labelling of cells and identifying as apoptotic cells, those being Annexin $V^+$ and $PI^-$.

In a preferred embodiment, $X_{4a}$ is valine;

$X_{4b}$ is aspartic acid;

$X_5$ is phenylalanine;

and $X_6$ is histidine.

Cell Penetrating Peptides:

In preferred embodiments, the pro-apoptotic peptide is linked with at least one cell penetrating peptide, forming a chimeric peptide construct.

Preferably the pro-apoptotic peptide is fused at the C-term of the penetrating peptide.

In a particular embodiment, the pro-apoptotic peptide may be linked to two, three or more penetrating peptides.

Preferably, the cell penetrating peptide comprises or consists of:

```
                                  (SEQ ID NO: 4)
a) X1-KKKIK-Ψ-EI-X2-X3
```

Wherein $X_1$ is vacant, is a lysine residue, or valine-lysine;

$X_2$ is vacant, is a lysine residue, or lysine-isoleucine;

$X_3$ is vacant or is an amino acid sequence of one to 4 amino acids;

and ψ is any amino-acid;

or a proteolysis-resistant peptide deriving from SEQ ID NO:4 by one or more chemical modifications, or a substantially homologous peptide, especially peptides deriving from SEQ ID NO:4 by one or more conservative substitutions.

b) $(RQKRLI)_3$ (SEQ ID NO: 5), $(RHSRIG)_3$ (SEQ ID NO: 6), RHSRIGIIQQRRTRNG (SEQ ID NO: 7), RHSRIGVTRQRRARNG (SEQ ID NO: 8), RRRRRRRSRGRRRTY (SEQ ID NO: 9), or homologous peptides;

c) Tat peptide, polyarginines peptide, HA2-$R_9$ peptide, Penetratin peptide (Antenna pedia), Transportan peptide, Vectocell® peptide, maurocalcine peptide, decalysine peptide, HIV-Tat derived PTD4 peptide, Hepatitis B virus Translocation Motif (PTM) peptide, $mPrP_{1-28}$ peptide, POD, pVEC, EB1, Rath, CADY, Histatin 5, Antp peptide, $Cyt^{86-101}$ peptide.

In an embodiment, in the cell penetrating peptide of a), X3 is vacant, i.e. the cell penetrating peptide is X1-KKKIK-ψ-EI-X2 (SEQ ID NO: 37).

In another embodiment, in the cell penetrating peptide of a), X1 is VK, X2 is KI and X3 is vacant, i.e. the cell penetrating peptide is VKKKKIK-ψ-EIKI (SEQ ID NO: 38).

Preferably ψ is arginine, lysine, asparagine, or alanine.

The cell-penetrating peptide can thus be VKKKKIKREIKI (SEQ ID NO:39), VKKKKIKAEIKI (SEQ ID NO:40), VKKKKIKKEIKI (SEQ ID NO:41) or VKKKKIKNEIKI (SEQ ID NO:42).

By "Tat peptide", it is meant a peptide having the sequence RKKRRQRRR (SEQ ID NO: 10, Tat peptide 2) or YGRKKRRQRRR, (SEQ ID NO: 11).

By "polyarginines peptide", it is meant a peptide consisting of at least 9 arginines. Preferably, a polyarginine peptide is a peptide having the sequence $R_9$ (SEQ ID NO: 12) or $R_{11}$ (SEQ ID NO: 13).

By "HA2-$R_9$ peptide", it is meant a peptide having the sequence GLFEAIEGFIENGWEGMIDGWYG-$R_9$ (SEQ ID NO: 14).

By "Penetratin peptide", it is meant a peptide having the sequence RQIKIWFQNRRMKWKK (SEQ ID NO: 15).

By "Transportan peptide" (also called "Antp peptide"), it is meant a peptide having the sequence GWTLNSAGYLLGKINLKALAALAKKIL (SEQ ID NO: 16).

By "Vectocell® peptide", it is meant a peptide originating from human heparin binding proteins and/or anti-DNA antibodies.

By "Maurocalcine peptide", it is meant a peptide having the sequence GDCLPHLKLCKENKDCCSKKCKRRGTNIEKRCR (SEQ ID NO: 17).

By "decalysine peptide", it is meant a peptide having the sequence KKKKKKKKKK ($K_{10}$) (SEQ ID NO: 18).

By "HIV-Tat derived PTD4 peptide", it is meant a peptide having the sequence YARAAARQARA (SEQ ID NO: 19).

By "Hepatitis B virus Translocation Motif (PTM) peptide", it is meant a peptide having the sequence PLSSIFSRIGDP (SEQ ID NO: 20).

By "$mPrP_{1-28}$ peptide", it is meant a peptide having the sequence MANLGYWLLALFVTMWTDVGLCKKRPKP (SEQ ID NO: 21).

By "POD peptide", it is meant a peptide having the sequence $GGG(ARKKAAKA)_4$ (SEQ ID NO: 22).

By "pVEC peptide", it is meant a peptide having the sequence LLIILRRRRIRKQAHAHSK (SEQ ID NO: 23).

By "EB1 peptide", it is meant a peptide having the sequence LIRLWSHLIHIWFQNRRLKWKKK (SEQ ID NO: 24).

By "Rath peptide", it is meant a peptide having the sequence TPWWRLWTKWHHKRRDLPRKPE (SEQ ID NO: 25).

By "CADY peptide", it is meant a peptide having the sequence GLWRALWRLLRSLWRLLWRA (SEQ ID NO: 26).

By "Histatin 5 peptide", it is meant a peptide having the sequence DSHAKRHHGYKRKFHEKHHSHRGY (SEQ ID NO: 27).

By "$Cyt^{86-101}$ peptide", it is meant a peptide having the sequence KKKEERADLIAYLKKA (SEQ ID NO: 28).

Chimeric Constructs:

A chimeric peptide construct according to the invention induces cell apoptosis, in vitro and/or in vivo. In particular, it induces apoptosis in xenograft models of breast cancer.

The chimeric peptide construct may preferably have a length comprised between 17 to 80 amino acids, preferably between 20 to 70 amino acids, still preferably between 23 to 40 amino acids.

In a preferred embodiment, the chimeric peptide construct is selected from the group consisting of:

```
                              (SEQ ID NO: 29)
VKKKKIKREIKI-YVETLDDIFEQWAHSEDL

                              (SEQ ID NO: 30)
VKKKKIKREIKI-YIETLDDILEQWARSEDL

                              (SEQ ID NO: 31)
VKKKKIKAEIKI-YVETLDDIFEQWAHSEDL

                              (SEQ ID NO: 32)
VKKKKIKAEIKI-YIETLDDILEQWARSEDL

                              (SEQ ID NO: 33)
VKKKKIKKEIKI-YVETLDDIFEQWAHSEDL

                              (SEQ ID NO: 34)
VKKKKIKKEIKI-YIETLDDILEQWARSEDL
```

-continued

```
                                 (SEQ ID NO: 35)
VKKKKIKNEIKI-YVETLDDIFEQWAHSEDL
or

                                 (SEQ ID NO: 36)
VKKKKIKNEIKI-YIETLDDILEQWARSEDL
```

or homologous or proteolysis-resistant peptides deriving thereof.

Peptide Preparation:

Peptides described herein can be synthesized using standard synthetic methods known to those skilled in the art, for example chemical synthesis or genetic recombination. In a preferred embodiment, peptides are obtained by stepwise condensation of amino acid residues, either by condensation of a preformed fragment already containing an amino acid sequence in appropriate order, or by condensation of several fragments previously prepared, while protecting the amino acid functional groups except those involved in peptide bond during condensation. In particular, the peptides can be synthesized according to the method originally described by Merrifield.

Examples of chemical synthesis technologies are solid phase synthesis and liquid phase synthesis. As a solid phase synthesis, for example, the amino acid corresponding to the C-terminus of the peptide to be synthesized is bound to a support which is insoluble in organic solvents, and by alternate repetition of reactions, one wherein amino acids with their amino groups and side chain functional groups protected with appropriate protective groups are condensed one by one in order from the C-terminus to the N-terminus, and one where the amino acids bound to the resin or the protective group of the amino groups of the peptides are released, the peptide chain is thus extended in this manner. Solid phase synthesis methods are largely classified by the tBoc method and the Fmoc method, depending on the type of protective group used. Typically used protective groups include tBoc (t-butoxycarbonyl), Cl—Z (2-chlorobenzyloxycarbonyl), Br—Z (2-bromobenzyloxycarbonyl), Bzl (benzyl), Fmoc (9-fluorenylmethoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and Clz-Bzl (2,6-dichlorobenzyl) for the amino groups; NO2 (nitro) and Pmc (2,2,5,7,8-pentamethylchromane-6-sulphonyl) for the guanidino groups); and tBu (t-butyl) for the hydroxyl groups). After synthesis of the desired peptide, it is subjected to the de-protection reaction and cut out from the solid support. Such peptide cutting reaction may be carried with hydrogen fluoride or tri-fluoromethane sulfonic acid for the Boc method, and with TFA for the Fmoc method.

Alternatively, the peptide may be synthesized using recombinant techniques. In this case, a nucleic acid and/or a genetic construct, comprising or consisting of a nucleotidic sequence encoding a peptide according to the invention, polynucleotides with nucleotidic sequences complementary to one of the above sequences and sequences hybridizing to said polynucleotides under stringent conditions.

The invention further relates to a genetic construct consisting of or comprising a polynucleotide as defined herein, and regulatory sequences (such as a suitable promoter(s), enhancer(s), terminator(s), etc.) allowing the expression (e.g. transcription and translation) of a peptide according to the invention in a host cell.

Thus, in another aspect, the invention relates to a host or host cell that expresses (or that under suitable circumstances is capable of expressing) a peptide of the invention; and/or that contains a polynucleotide of the invention or genetic construct of the invention.

The method of producing the peptide may optionally comprise the steps of purifying said peptide, chemically modifying said peptide, and/or formulating said peptide into a pharmaceutical composition.

Further Protection Against Proteolysis:

The N- and C-termini of the peptides described herein may be optionally protected against proteolysis. For instance, the N-terminus may be in the form of an acetyl group, and/or the C-terminus may be in the form of an amide group. Internal modifications of the peptides to be resistant to proteolysis are also envisioned, e.g. wherein at least a —CONH-peptide bond is modified and replaced by a (CH2NH) reduced bond, a (NHCO) retro-inverso bond, a (CH2-O) methylene-oxy bond, a (CH2-S) thiomethylene bond, a (CH2CH2) carba bond, a (CO—CH2) cetomethylene bond, a (CHOH—CH2) hydroxyethylene bond), a (N—N) bound, a E-alcene bond or also a —CH═CH-bond.

For instance the peptide may be modified by acetylation, acylation, amidation, crosslinking, cyclization, disulfide bond formation, formation of covalent cross-links, formation of cysteine, formation of pyroglutamate, formylation, gamma-carboxylation, glycosylation, GPI anchor formation, hydroxylation, iodination, methylation, myristylation, oxidation, phosphorylation, and the like.

The peptides of the invention may be composed of amino acid(s) in D configuration, which render the peptides resistant to proteolysis. They may also be stabilized by intramolecular crosslinking, e.g. by modifying at least two amino acid residues with olefinic side chains, preferably C3-C8 alkenyl chains, preferably penten-2-yl chains) followed by chemical crosslinking of the chains, according to the so-called "staple" technology described in Walensky et al, 2004. For instance, amino acids at position i and i+4 to i+7 can be substituted by non-natural aminoacids that show reactive olefinic residues. All these proteolysis-resistant chemically-modified peptides are encompassed in the present invention.

In another aspect of the invention, peptides are covalently bound to a polyethylene glycol (PEG) molecule by their C-terminal terminus or a lysine residue, notably a PEG of 1500 or 4000 MW, for a decrease in urinary clearance and in therapeutic doses used and for an increase of the half-life in blood plasma. In yet another embodiment, peptide half-life is increased by including the peptide in a biodegradable and biocompatible polymer material for drug delivery system forming microspheres. Polymers and copolymers are, for instance, poly(D,L-lactide-co-glycolide) (PLGA) (as illustrated in US2007/0184015, SoonKap Hahn et al).

Nucleic Acids

The invention also relates to a polynucleotide comprising or consisting of a nucleotide sequence encoding a peptide according to the invention.

The invention further relates to a genetic construct consisting of or comprising a polynucleotide as defined herein, and regulatory sequences (such as a suitable promoter(s), enhancer(s), terminator(s), etc.) allowing the expression (e.g. transcription and translation) of a peptide according to the invention in a host cell.

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting aspect, a genetic construct of the invention comprises i) at least one nucleic acid of the invention; operably connected to ii) one or more regulatory elements, such as a promoter and optionally a suitable terminator; and optionally also iii) one or more further elements of genetic constructs such as 3'- or 5'-UTR sequences, leader sequences, selection markers, expression markers/reporter genes, and/or elements that may facilitate or increase (the efficiency of) transformation or integration.

In a particular embodiment, the nucleic acid encoding the cell-penetrating peptide of the invention is coupled or fused to a nucleic acid that encodes a peptide or protein of interest. The peptide of interest may be a pro-apoptotic peptide as described herein. More generally it may the peptide or protein of interest may be any peptide or protein to express, such as therapeutic peptide or polypeptide, as well as any antigenic or immunogenic peptide if desired.

The nucleic acid may especially be carried by a viral vector, such as an adenovirus or a lentivirus, for ex vivo or in vivo infection and expression of the chimeric peptide construct.

Anti-Tumor Adjuvant Therapy:

The chimeric peptides as defined herein, or nucleic acids that encode said peptides, are useful as adjuvants in anti-tumor therapy.

The adjuvant therapy of the invention is helpful in eradicating any persistent microscopic malignancy, and/or preventing or delaying relapses.

Furthermore, the chimeric peptides (or nucleic acids that encode said peptides) may be used for preventing or treating metastases.

It is thus described a method of treatment of a tumor in a patient in need thereof, which method comprises administering said patient with the chimeric peptide construct, or a nucleic acid encoding said construct, in combination with an anti-tumor agent, preferably a chemotherapeutic agent.

The "anti-tumor agent" include conventional cytotoxic chemotherapies with inhibitors of DNA replication such as DNA binding agents in particular alkylating or intercalating drugs, antimetabolite agents such as DNA polymerase inhibitors, or topoisomerase I or II inhibitors, or with anti-mitogenic agents such as alkaloids. It also includes protease (kinase, aromatase, ATPase) inhibitors, monoclonal antibodies or hormones or hormone analogs.

In a preferred embodiment, the anti-tumor agent may be any chemotherapeutic agent, including paclitaxel, docetaxel, carboplatin, cisplatin, other platins, doxorubicin, epirubicin, cyclophosphamide, iphosphamide, gemcitabine, capecitabine, vinorelbine, topotecan, irinotecan, tamoxifen, camptothecins, 5-fluorouracile (5-FU), EMP, etoposide, methotraxate and the like.

Preferably, the agent is doxorubicin or cyclophosphamide, or a combination thereof.

In other preferred embodiments, the agent may be docetaxel, 5-FU, or cisplatin.

In a further embodiment, the anti-tumor agent may be a hormone or a hormone analog, including progestogens such as megestrol acetate and medroxyprogesterone acetate, androgens, such as fluoxymesterone, or estrogens, such as diethylstilbestrol (DES), or somatostatin analogs such as octreotide, as well as analogs of gonadotropin-releasing hormone (GnRH).

The peptides (or nucleic acids that encode said peptides) described herein are useful for the treatment of a tumor, in particular a cancer tumor, preferably in a human patient.

The tumor may be cancer, such as a haematologic cancer, in particular acute myelogenous leukaemia (AML), chronic lymphocytic leukaemia (CLL), multiple myeloma, Hodgkin's disease, non-Hodgkin's lymphoma, B cell, cutaneous T cell lymphoma, or a non-haematologic cancer, for instance brain, epidermoid (in particular lung, breast, ovarian), head and neck (squamous cell), bladder, gastric, pancreatic, head, neck, renal, prostate, colorectal, oesophageal or thyroid cancer, and melanoma.

Different types of cancers may include, but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, lymphoma, leukemia, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma, uveal melanoma and breast cancer.

More particularly the peptides described herein (or nucleic acids that encode said peptides) are useful in the treatment of cancers which exhibit a deregulation of PP1 and/or PP2A or which exhibit an over-expression of the anti-apoptotic protein Bcl-2, an apoptotic regulator that interacts with and is controlled by PP1 and PP2A.

High levels of expression of the human bcl-2 gene have been found in all lymphomas with t (14; 18) chromosomal translocations including most follicular B cell lymphomas and many large cell non-Hodgkin's lymphomas. High levels of expression of the bcl-2 gene have also been found in leukemias that do not have a t (14; 18) chromosomal translocation, including lymphocytic leukemias of the pre-B cell type, neuroblastomas, nasophryngeal carcinomas, and many adenocarcinomas of the prostate, breast, and colon. Especially overexpression of bcl-2 was found in chronic lymphocytic leukemia (CLL) (Deng et al, 2009; Prickett et al, 2004).

In a preferred embodiment, the cancer tumor is thus a lymphoma, especially a leukemia, such as chronic lymphocytic leukemia (CLL).

In another preferred embodiment, the cancer tumor is a breast cancer.

Preferably, the agent is doxorubicin or cyclophosphamide, or a combination thereof, and the human patient is affected with a breast cancer.

Pharmaceutical Compositions:

The chimeric peptides (or nucleic acid that encodes said peptide) may be administered by any convenient route including intravenous, oral, transdermal, subcutaneous, mucosal, intramuscular, intrapulmonary, intranasal, parenteral, rectal, vaginal and topical. Intranasal route is of particular interest.

Advantageously, intra-tumoral administration is also contemplated.

The chimeric peptides (or nucleic acid that encodes said peptide) are formulated in association with a pharmaceutically acceptable carrier.

The pharmaceutical composition may also include any other active principle, such as in particular an anti-cancer agents, e.g. conventional cytotoxic chemotherapies with inhibitors of DNA replication such as DNA binding agents in particular alkylating or intercalating drugs, antimetabolite agents such as DNA polymerase inhibitors, or topoisomerase I or II inhibitors, or with anti-mitogenic agents such as alkaloids.

In a preferred embodiment, the chimeric peptides (or nucleic acid that encodes said peptide) may be administered by electroporation. Electroporation, also known as electropermeabilization or electroinjection, is the permeabilization of cell membranes as a consequence of the application of certain short and intense electric fields across the cell membrane, the cells or the tissues. Typically, electroporation consists of injecting compounds, preferably via intramuscular or intradermal route, followed by applying a series of electric pulses by means of electrodes connected to a generator. The conditions for applying an electric field in the injection zone are now well known to those persons skilled in the art, and are in particular described in the U.S. Pat. No. 5,468,223. Those persons skilled in the art will be able to adapt these conditions according to each case. The electric field may be 50-200 microseconds pulses of high-strength electric fields in the range of 1-5000 V/cm and with a frequency between 0.1 and 1,000 hertz. Typically, a sequence of eight 100 microseconds pulses of 1000-1500 V/cm with a frequency of 1 hertz is applied.

The preparation of a pharmacological composition that contains active ingredients dissolved or dispersed therein is well understood in the art and need not be limited based on formulation. Typically such compositions are prepared as injectables either as liquid solutions or suspensions; however, solid forms suitable for solution, or suspensions, in liquid prior to use can also be prepared. The preparation can also be emulsified. In particular, the pharmaceutical compositions may be formulated in solid dosage form, for example capsules, tablets, pills, powders, dragees or granules.

The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

Preparation can involve the formulation of the desired molecule with an agent, such as injectable microspheres, bioerodible particles, polymeric compounds (such as polylactic acid or polyglycolic acid), beads or liposomes, that may provide controlled or sustained release of the product.

The dosing is selected by the skilled person so that a pro-apoptotic effect is achieved, and depends on the route of administration and the dosage form that is used. Total daily dose of chimeric peptides (or nucleic acid that encodes said peptide) administered to a subject in single or divided doses may be in amounts, for example, of from about 0.001 to about 100 mg/kg body weight daily and preferably 0.01 to 10 mg/kg/day. A daily dosage of about 5 mg/kg is preferred. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

Protocols:

The adjuvant peptide (or nucleic acid that encodes said peptide) and the anti-tumor agent, which is preferably a chemotherapeutic agent, are intended for simultaneous administration (i.e., at the same time, as a single composition or separate compositions), or sequential administration (i.e. the agent is administered prior to the adjuvant or vice versa).

In a preferred embodiment, the peptide construct (or nucleic acid that encodes said peptide) is intended for administration at the end or after the end of the treatment with the anti-tumor agent, which is preferably a chimiotherapeutic agent, whereby relapses are prevented.

In a preferred embodiment, the peptide construct (or nucleic acid that encodes said peptide) is intended for administration after a period of about 5 to about 30 days, preferably from about 7 to about 20 days, after the anti-tumor agent, which is preferably a chemotherapeutic agent, is administered.

Preferably the peptide construct (or nucleic acid that encodes said peptide) is administered once a day during a period of at least one week, preferably at least two weeks.

Further aspects and advantages of the present invention will be disclosed in the following experimental section, which should be regarded as illustrative and not limiting the scope of the present application.

LEGENDS TO THE FIGURES

FIG. 1 is a graph that shows relative tumor volume in mice bearing a xenograft of BC146 human breast cancer model.

Figure 2:
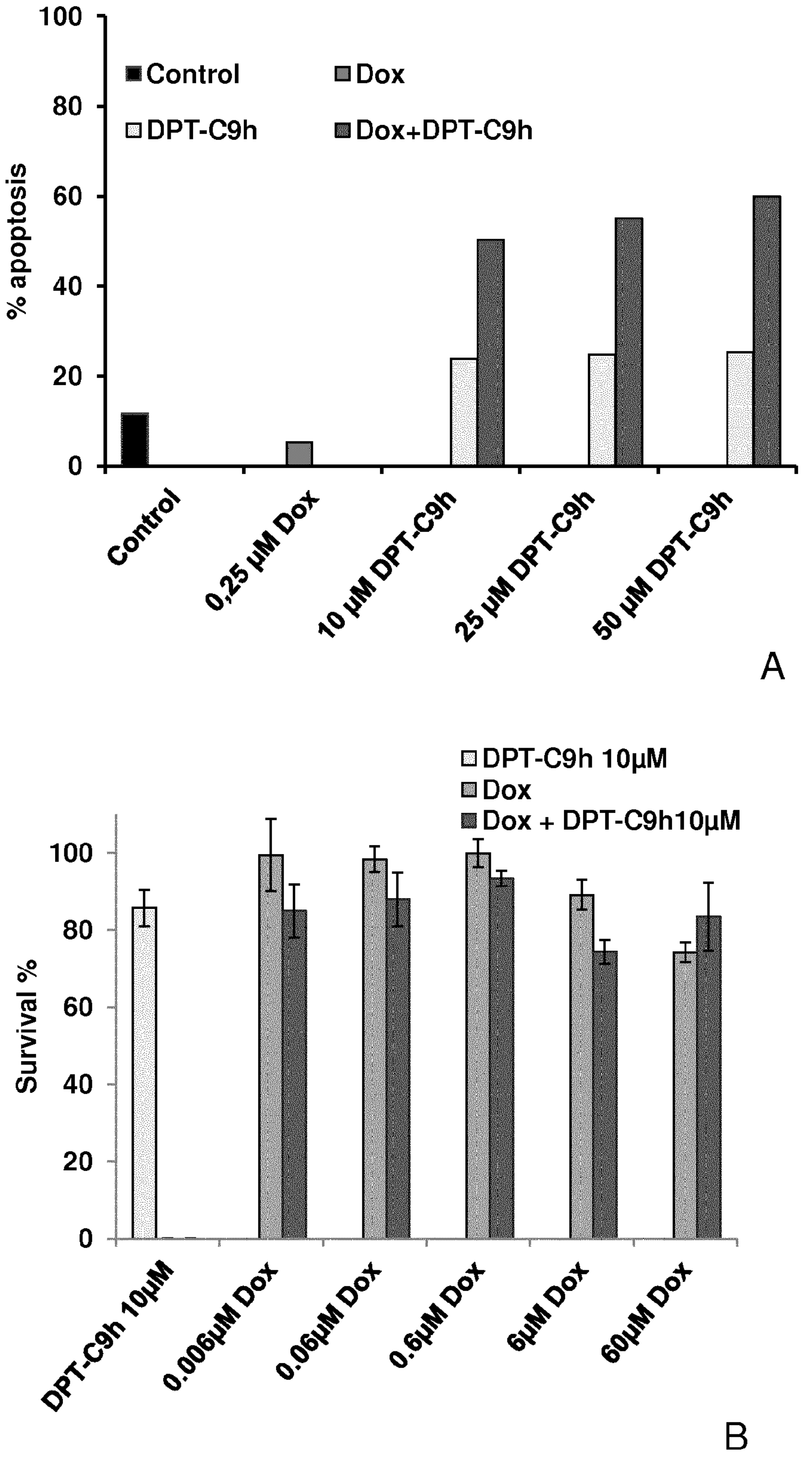

FIGS. 2A and 2B show in vitro apoptotic effect of DPT-C9h and doxorubicin. FIG. 2A) MDA MB 231 cells were cultured in the presence of different doses of doxorubicin for 24 h and then, apoptosis was estimated by annexin staining. FIG. 2B) Cells were cultured in the presence of doxorubicin, different doses of peptide or the combination of both for 24 h and then apoptosis was estimated by annexin staining.

Figure 3:
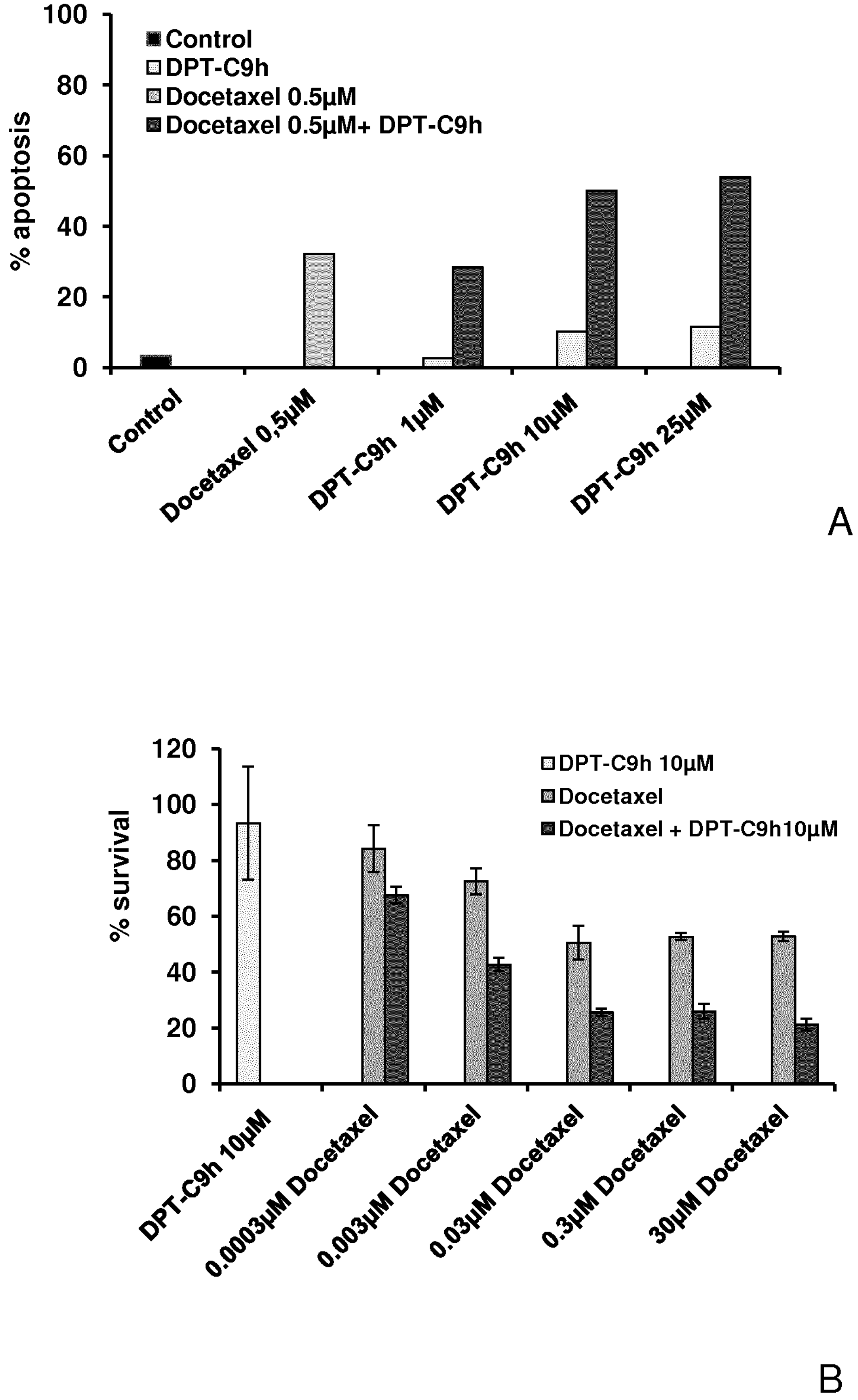

FIGS. 3A and 3B apoptotic effect of docetaxel alone or combined with DPT-C9h. FIG. 3A) Cells were cultured in the presence of a dose of docetaxel (0.5 μM), different doses of peptide or the combination of both for 24 h. After this period of time, apoptosis was estimated as above. FIG. 3B) Cells were cultured for 61 h in the presence of different doses of docetaxel and one single dose of DPT-C9h peptide (10 μM Cell survival was estimated by MTT colorimetric test.

Figure 4:
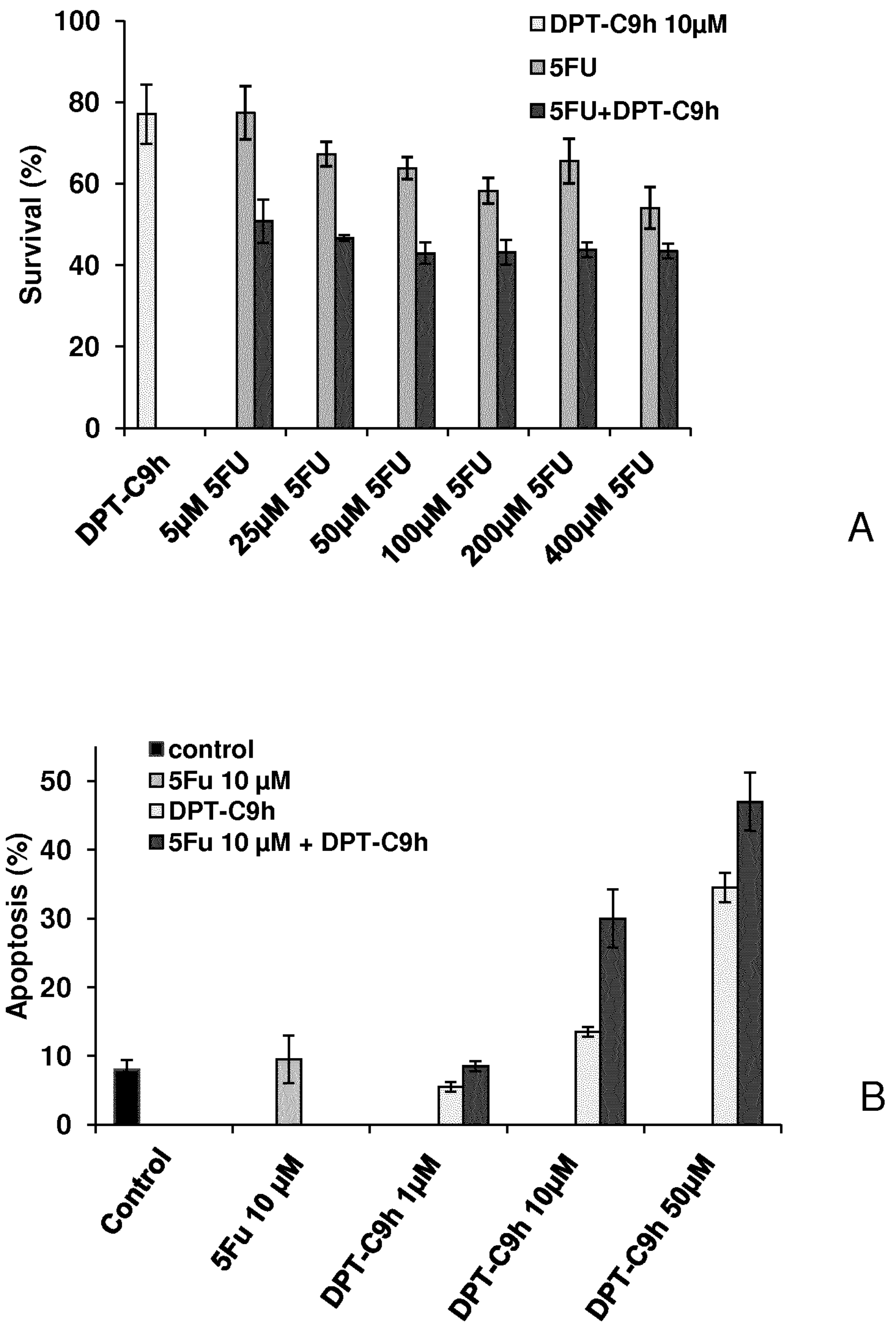

FIGS. 4A and 4B shows in vitro effect of 5FU and DPT-C9h peptide treatment FIG. 4A) MDA MB 231 cells were cultured for 24 h in the presence of 10 μM of 5FU and then, different doses of DPT-C9h peptide were added for 24 supplementary hours. After this period, apoptosis was estimated by annexin staining. FIG. 4B) Cells were cultured for 61 h in the presence of different doses of 5FU and one single dose of DPT-C9h peptide (10 μM). Cell survival was estimated by MTT colorimetric test.

Figure 5:
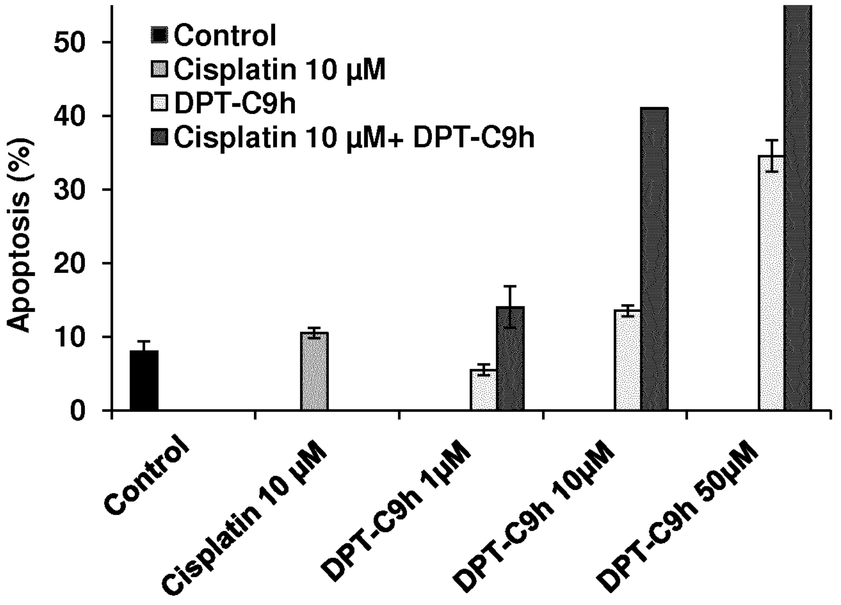
Figure 5:
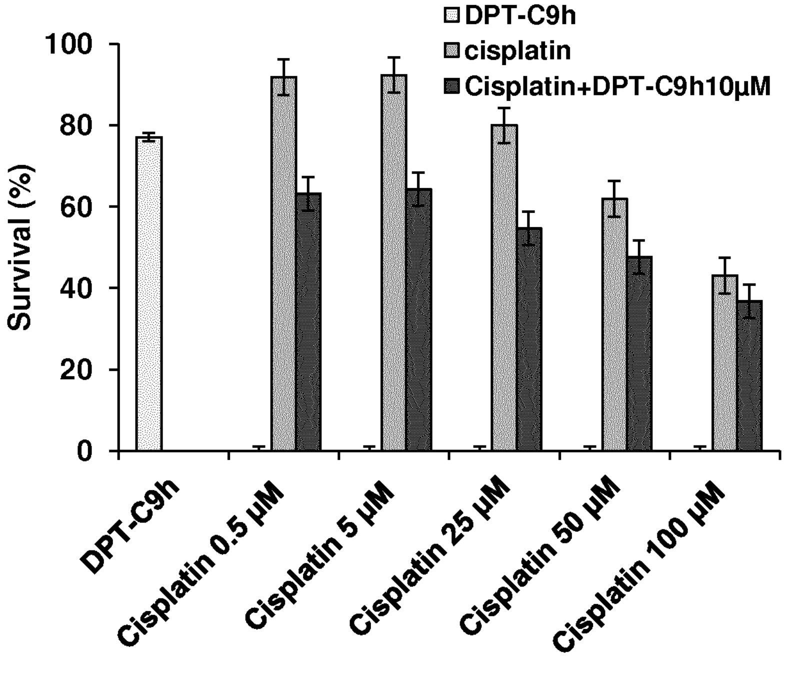

FIGS. 5A and 5B show apoptotic effect of cisplatin, alone or combined with DPT-C9h. FIG. 5A) MDA MB 231 cells were cultured for 24 h in the presence of 10 μM of cisplatin and then, different doses of DPT-C9h peptide were added for 24 supplementary hours. After this period or time, apoptosis was estimated by annexin staining. FIG. 5B) Cells were cultured for 61 h in the presence of different doses of cisplatin and one single dose of DPT-C9h peptide (10 μM) Cell survival was estimated by MTT colorimetric test.

EXAMPLES

Example 1

Effects of Combined Treatment with DPT-C9h or DPT-C9 and Chemotherapy (Cyclophosphamide-Doxorubicine)

1.1. Materials and Methods

Peptide Synthesis and Sequence

Peptides were synthesized in an automated multiple peptide synthesizer with solid phase procedure and standard Fmoc chemistry. The purity and composition of the peptides were confirmed by reverse phase HPLC and by amino acid analysis.

```
                                              (SEQ ID NO: 29)
DPT-C9h is VKKKKIKREIKI-YVETLDDIFEQWAHSEDL,

                                              (SEQ ID NO: 30)
DPT-C9 is VKKKKIKREIKI-YIETLDDILEQWARSEDL,
```

In Vivo Models of Primary Human Tumor Xenografts

The primary human xenografts were obtained as previously described (Marangoni et al., 2007). Mouse breast cancer tumors were obtained using the transgenic Polyoma Middle-T Mouse PyMT model. Spontaneously growing mammary tumors occurring in transgenic mice were xenografted into nude immunodeficient mice to allow pharmacological assessments, and maintained from nude mouse to nude mouse serially passages.

Therapeutic Assays

For therapeutic experimental assays, 5- to 8-week old Swiss nu/nu female mice received a subcutaneous graft of tumor fragments with a volume of approximately 15 mm3. Tumors developed at the graft site 2 to 6 weeks later. Mice bearing growing tumors with a volume of 40 to 200 $mm^3$ were individually identified and randomly assigned to the control or treatment groups (10 animals in each group) and treatments were started on day 1. Mice were weighed twice a week. Tumour-bearing mice were sacrificed when the tumor volume reached 2500 $mm^3$, defined as the ethical limit. Tumor volumes and antitumor activity were evaluated as previously reported (Nemati et al. 2009. Anti Cancer Drugs 20, pages 932-940).

DPT-C9h peptide diluted in water/glucose (1 to 25 mg/kg) was given by intraperitoneally route 5 to 7 days per week, according to the models and the therapeutic schedules. Doxorubicin (Teva Pharmaceuticals) and cyclophosphamide (Baxter) were diluted in 0.9% NaCl and administered intraperitoneally at a dose of 2 mg/kg and 100 mg/kg at day 1, respectively.

1.2. Results

DPT-C9h and DPT-C9 induce in vivo tumor growth inhibition of primary human and mouse breast cancer xenograft and synergize with cyclophosphamide-doxorubicine chemotherapy.

The anti-tumoral effect of DPT-C9h was tested in mice bearing breast cancer model BC52 and BC146. DPT-C9h was intraperitoneally administered at 5 mg/kg once daily for 5 weeks. At the end of the treatment, the inventors observed that DPT-C9h induces significant tumor growth inhibition (Table 4).

The anti-tumoral effect of the mouse peptide DPT-C9 was analyzed in nude mice bearing xenograft mouse breast tumors obtained from the transgenic polyoma Middle-T mice. PyMT model was treated with the mouse specific DPT-C9 peptide, which was intraperitoneally administrated daily at a dose of 5 mg/kg. DPT-C9 also induces significant tumor growth inhibition.

The inventors have further tested combined administration of DPT-C9h with doxorubicin and cyclophosphamid chemotherapy. The administration was either simultaneous or sequential: DPT-C9h was then administered at day 20, a stage corresponding to a chemotherapy-induced complete remission. The inventors have observed that DPT-C9h delayed tumor relapse better than chemotherapy alone (Table 4, FIG. 1).

TABLE 4

Effect of combined addition of DPT-C9h peptide and chemotherapy

| Models | Treatment | Criteria | Control | DPT-C9h | Chemo. | Chemo. + DPT-C9h | Chemo. then DPT-C9h |
|---|---|---|---|---|---|---|---|
| BC52 | Ovariectomy | RTV | 1.89 | 0.70 | 0.75 | 0.89 | — |
| | | OS | 10% | 33% | 56% | 78% | — |
| | Doxorubicin + cyclophosphamid | CR | 0/10 | 0% | 100% | 100% | 100% |
| BC146 | | Relapses | — | — | 5/9 | 4/9 | 4/10 |
| | | RTV | 30.6 | 20.2 | 1.54 | 1.06 | 0.45 |
| | | OS | 0% | 27% | 89% | 100% | 100% |

RTV: Relative tumor volume, OS: Overall survival, CR: Complete remission
Chemo: chemotherapy
—: not determined

Example 2

Effects of Combined Treatment with DPT-C9h and Chemotherapy (Doxorubicin, Docetaxel, 5FU and Cisplatin)

Resistance to cell death induction has been recognized as a hallmark of cancer. It is herein propose to combine very low doses of chemotherapy with a chimeric peptide DPT-C9h to induce apoptosis of tumor cells avoiding the side effects of high doses of chemotherapy.

2.1. Materials and Methods

Cells

MDA MB231 breast cancer cell line was cultured in DMEM medium supplemented with 10% of FCS.

Peptide Synthesis and Sequence

Peptide DPT-C9h was synthesized in an automated multiple peptide synthesizer with solid phase procedure and standard Fmoc chemistry. The purity and composition of the peptide was confirmed by reverse phase HPLC and by amino acid analysis.

Detection of Apoptosis by Annexin-V-FITC Staining

Apoptotic cells were detected using Annexin-V (-FITC from BD biosciences) as described by the manufacturer. Briefly, the cells were washed in 1× binding buffer, centrifuged and then resuspended in 200 μl of 1× binding buffer containing Annexin V-FITC (0.1 μg/ml) and PI (0.5 μg/ml). After incubation at room temperature in the dark for 10 min, cells were analyzed by flow cytometry. Data acquired by FACSCalibur (BD biosciences) were analyzed with Cellquest Pro software.

Cytotoxicity Assay

The cytotoxicity of chemotherapy and the peptide was assessed by MTT. Cells were in contact with various treatments for 72 h. Cells were rinsed with culture medium and incubated with 10 μl MTT (5 mg/ml) in a final volume of 100 μl for 4 h at 37° C. The formation of blue formazan crystals was visualized by microscopy. After this period of incubation, 100 μl of 10% SDS in 10 mM HCl was added to each well and the plate incubated overnight. The absorbance was measured at 570 and 620 nm and the percentage of viable cells to untreated controls was estimated.

2.2. Results

DPT-C9h Synergizes with Doxorubicin, Docetaxel, 5FU and Cisplatin Chemotherapy

The apoptotic effect of DPT-C9h and chemotherapy was tested in the breast cancer cell line MDAMB231. FIG. 2A shows the apoptotic effect of doxorubicin alone upon 24 h of contact with the cells. We have selected a low dose of doxorubicin, 0.25 μM to combine with the peptide. FIG. 2B shows the apoptotic effect of the combination of different dose of DPT-C9h with the low dose of doxorubicin. The combination of both has a synergistic effect on apoptosis at all of the peptide doses tested.

The combined effect of DPT-C9h and docetaxel is shown in FIG. 3A. The inventors observed a synergistic apoptotic effect of a low dose of docetaxel in combination with 10 and 25 μM of DPT-C9h peptide. The survival of MDA MB231 cells cultured with different doses of docetaxel and a unique dose of peptide is shown in FIG. 3B. We observe a low survival of cells cultured in the presence of docetaxel and peptide compared to cells maintained only in the presence of docetaxel.

The inventors have further analyzed the combined effect of DPT-C9h peptide and 5FU (FIG. 4A). They detected a synergistic apoptotic effect by the combination of a low apoptotic dose of 5FU with 25 or 50 μM □ of DPT-C9h. This effect correlates with the low cell survival detected with the combination of both molecules (FIG. 4B).

Finally, they analyzed the effect of the combination of cisplatin and DPT-C9h peptide (FIG. 5A). Similarly, the inventors observed a synergistic apoptotic effect of the combined treatment of cisplatin and increasing doses of DPT-C9h. This effect also correlates with low level of cell survival when cisplatin is associated to DPT-C9h (FIG. 5B).

Taken together, these results show a synergistic apoptotic effect of the combination of low doses of chemotherapy (doxorubicin, docetaxel, 5FU and cisplatin) with peptide DPT-C9h.

REFERENCES

Deng X, Gao F, and W. Stratford May. Dephosphorylation and up-regulation of Bcl2-p53 binding Protein phosphatase 2A inactivates Bcl-2's antiapoptotic function by dephosphorylation and up-regulation of Bcl2-p53 binding. Blood. 2009 Jan. 8; 113(2):422-8.

Lehninger, (1975) Biochemistry, Second Edition, Worth Publishers, Inc. New-York: NY., pp. 71-77.

Marangoni et al., 2007. Clinical Cancer Research 13, pages 3989-3998.

Nemati et al. 2009. Anti Cancer Drugs 20, pages 932-940.

Prickett T D, and Brautigan D (2004). Overlapping binding sites in Protein Phosphatase 2A for association with regulatory 1 and a4 (mTap42) subunits. J. Biol. Chem. 279, 38912-38920.

Walensky et al, Science, 2004, 305:1466-1470

The invention claimed is:

1. A chimeric peptide construct for use in treating a tumor in combination with an anti-tumor agent, wherein the chimeric peptide construct is selected from the group consisting of:

(SEQ ID NO: 29)
VKKKKIKREIKI-YVETLDDIFEQWAHSEDL, (SEQ ID NO: 30)
VKKKKIKREIKI-YIETLDDILEQWARSEDL, (SEQ ID NO: 31)
VKKKKIKAEIKI-YVETLDDIFEQWAHSEDL, (SEQ ID NO: 32)
VKKKKIKAEIKI-YIETLDDILEQWARSEDL, (SEQ ID NO: 33)
VKKKKIKKEIKI-YVETLDDIFEQWAHSEDL, (SEQ ID NO: 34)
VKKKKIKKEIKI-YIETLDDILEQWARSEDL, (SEQ ID NO: 35)
VKKKKIKNEIKI-YVETLDDIFEQWAHSEDL,
and (SEQ ID NO: 36)
VKKKKIKNEIKI-YIETLDDILEQWARSEDL.

2. A method of treating a tumor, comprising administering to a subject in need thereof the chimeric peptide construct according to claim 1 and an anti-tumor agent, wherein the tumor is a cancer selected from the group consisting of acute myelogenous leukaemia, chronic lymphocytic leukaemia, multiple myeloma, Hodgkin's disease, non-Hodgkin's lymphoma, B cell, cutaneous T cell lymphoma, uveal melanoma, melanoma and brain, lung, breast, ovarian, head and neck, bladder, gastric, pancreatic, head, neck, renal, prostate, colorectal, oesophageal, and thyroid cancer.

3. The method of claim 2, wherein the chimeric peptide construct and the anti-tumor agent are sequentially administered.

4. The method of claim 2, wherein the anti-tumor agent is a chemotherapeutic agent.

5. The method of claim 4, wherein the chemotherapeutic agent is doxorubicin and/or cyclophosphamide.

6. The method of claim 4, wherein the chemotherapeutic agent is docetaxel, 5-FU, or cisplatin.

7. The method of claim 5, wherein the tumor is a breast cancer.

8. The method of claim 4, wherein the peptide construct is administered after a period of about 5 to about 30 days after the chemotherapeutic agent is administered.

9. A method of reducing the risk of relapse of a tumor, comprising administering to a subject in need thereof the chimeric peptide construct according to claim 1 and an anti-tumor agent.

* * * * *